United States Patent
Yamano et al.

(10) Patent No.: US 7,541,498 B2
(45) Date of Patent: Jun. 2, 2009

(54) PROCESS FOR PRODUCTION OF PHOSPHINE-BORANE COMPLEXES

(75) Inventors: Mitsuhisa Yamano, Osaka (JP); Mitsutaka Goto, Osaka (JP); Masatoshi Yamada, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 246 days.

(21) Appl. No.: 10/556,499

(22) PCT Filed: May 18, 2004

(86) PCT No.: PCT/JP2004/007032

§ 371 (c)(1),
(2), (4) Date: Nov. 10, 2005

(87) PCT Pub. No.: WO2004/101580

PCT Pub. Date: Nov. 25, 2004

(65) Prior Publication Data

US 2006/0199968 A1    Sep. 7, 2006

(30) Foreign Application Priority Data

May 19, 2003    (JP) .............................. 2003-140671

(51) Int. Cl.
C07F 9/50    (2006.01)
C07F 5/02    (2006.01)
(52) U.S. Cl. ......................................................... 568/2
(58) Field of Classification Search ...................... None
See application file for complete search history.

(56) References Cited

U.S. PATENT DOCUMENTS

2003/0166978 A1    9/2003    Tsutsumi et al.
2005/0027124 A1    2/2005    Goto et al.

FOREIGN PATENT DOCUMENTS

JP    2003206295    7/2003

OTHER PUBLICATIONS

Keglevich, G. et al. "Synthesis of phosphine-borane complexes of P-heterocycles", J. Organometallic Chemistry, (1996), 516, 139-145.*
Imamoto, T. et al. "Sterospecific Reduction of Phosphine Oxides to Phosphines by the Use of a Methylation Reagent and Lithium Aluminum Hydride", Organic Letters, (2001), 3(1), 87-90.*
Keglevich, G. et al., "Convenient method for the reduction of the double-bond of cyclic vinylphosphine oxides using borane" (2000) Synthetic Communications 30(23), 4221-4231.*
U. Schmidt, et al., "A Useful Synthesis of (R,R)-1,2-Ethanediylbis[(o-methoxyphenylphosphine] the Ligand of the Enantioselective Catalyst [Rh(COD) (DIPAMP)]+BF4", Synthesis, (1991), pp. 655-657.
G. Keglevich, et al., "Synthesis of Phosphine-Boraine Complexes of P-heterocycles", Journal of Organometallic Chemistry, (1996), vol. 516, pp. 139-145.
K. Shioji, et al., "Novel Synthesis of P-chiral Hydroxymethylphosphine-Boranes Through Lipase-Catalyzed Optical Resolution", Bull. Chem. Sox. Jpn., (2003), vol. 76, pp. 833-834.
European Search Report issued Dec. 4, 2008 in EP 04733647.4.
Stankevic, M. et al., "An Expedient Reduction of sec-Phosphine Oxides to sec-Phospine-boranes by $BH_3 \cdot SMe_2$", Synlett, (2003), No. 7: 1012-1016.

* cited by examiner

*Primary Examiner*—Daniel M Sullivan
*Assistant Examiner*—Yevegeny Valenrod
(74) *Attorney, Agent, or Firm*—Wenderoth, Lind & Ponack, L.L.P.

(57) ABSTRACT

A process for the production of phosphine-borane complexes represented by the general formula:

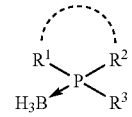

or salts thereof: [wherein $R^1$, $R^2$ and $R^3$ are each independently a hydrogen atom, a halogen atom, an optionally substituted alkyl group, an optionally substituted cycloalkyl group, an optionally substituted aryl group, or an optionally substituted heterocyclic group (with the proviso that $R^1$ and $R^2$ together with the adjacent phosphorus atom may form a 4- to 6-membered ring)], characterized by converting a compound represented by the general formula:

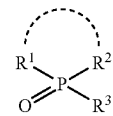

in a solvent in the presence of a borane reagent: [wherein each symbol is as defined above].

6 Claims, No Drawings

PROCESS FOR PRODUCTION OF PHOSPHINE-BORANE COMPLEXES

This application is the National Phase filing of International Patent Application No. PCT/JP2004/007032, filed May 18, 2004.

TECHNICAL FIELD

The present invention relates to a process for the production of phosphine-borane complexes.

BACKGROUND ART

Phosphine-borane complexes are compounds which are generally not decomposed in air or water, but easily converted into phosphines by release of borane with an amine and therefore have been used for synthesis of many organic phosphorus compounds as the equivalent to phosphines. For example, the following reaction scheme of a synthesis method of 1,2-bis[(o-anisyl)phenylphosphino]ethane (DI-PAMP) as a ligand useful for an asymmetric reduction is described in Heteroatom Chemistry, No. 3, p. 563-575, 1992.

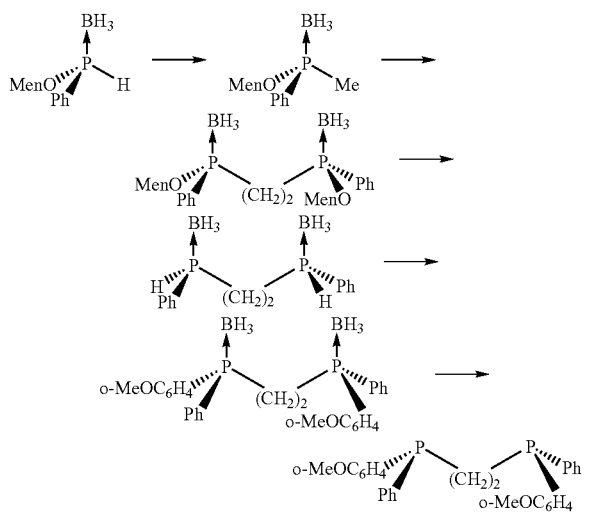

Also, Tetrahedron Letters, No. 40. p. 201-204, 1999 reports that triarylphosphines are synthesized by reaction with aryltriflate in the presence of a palladium catalyst.

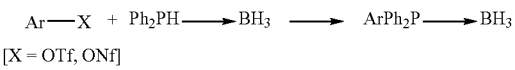

As processes for producing phosphine-borane complexes the following processed are reported:

1) a method for obtaining a phosphine-borane complex by reaction of a phosphine oxide in the presence of cerium chloride, sodium borohydride, and lithium aluminum hydride (Journal of the American Chemical Society, No. 107, p. 5301-5303, 1985);
2) a method for obtaining a phosphine-borane complex by reaction of a phosphine oxide in the presence of methyltriflate, lithium aluminum hydride, and a borane-tetrahydrofuran complex (Organic Letters, No. 3, p. 87-90, 2001);
3) a method for obtaining a phosphine-borane complex by reaction of a phosphine as a starting material with a borane-tetrahydrofuran complex (Angewandte Chemie International Edition, No. 18, p. 781-782, 1979);
4) a method for obtaining a phosphine-borane complex by reaction of a chlorophosphine as a starting material with lithium aluminum hydride and a borane-tetrahydrofuran complex (Journal of the American Chemical Society, No. 112, p. 5244-5252, 1990);
5) a method for obtaining a phosphine-borane complex by reaction of a phosphine oxide in the presence of diethylborane (Chemische Berichte, No. 120, p. 1117-1123, 1987); and
6) a method for obtaining a phosphine-borane complex by reaction of a cyclic phosphine oxide in the presence of a borane-dimethylsulfide complex (Journal of the Chemical Society, Perkin Transactions 1, p. 4451-4455, 2000).

DISCLOSURE OF THE INVENTION

Since trivalent organic phosphorus compounds liable to be oxidized and unstable are used as reaction reagents in the above-mentioned methods 3) and 4), and lithium aluminum hydride is used as a reducing agent in the above-mentioned 1), 2) and 4), respectively, the purification becomes complicated and there is a problem in the safety. In the synthesis method of 5), it is difficult to selectively obtain only the phosphine-borane complex and, in the case of the method 6), only a synthesis example of the cyclic phosphine-borane complex is reported.

The present inventors have studied processes for producing phosphine-borane complexes to be used for synthesis of organic phosphorus compounds, intensively, and have found that, when the reaction of a compound represented by the formula (II):

wherein $R^1$, $R^2$, and $R^3$ are the same or different and independently represent a hydrogen atom, a halogen atom, an optionally substituted alkyl group, an optionally substituted cycloalkyl group, an optionally substituted aryl group, or an optionally substituted heterocyclic group with the proviso that $R^1$ and $R^2$ together with the adjacent phosphorus atom may form a 4- to 6-membered ring (hereinafter, abbreviated as compound (II) in some cases), or a salt thereof is carried out for the first time in a solvent in the presence of a borane reagent, a phosphine-borane complex represented by the formula (I):

wherein each symbol is as defined above (hereinafter, abbreviated as compound (I) in some cases), or a salt thereof is obtained in a high yield under mild conditions. The present invention has been completed based on the finding.

That is, the present invention relates to:

(1) A process producing a phosphine-borane complex represented by the formula:

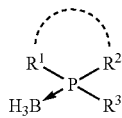

wherein $R^1$, $R^2$, and $R^3$ are the same or different and independently represent a hydrogen atom, a halogen atom, an optionally substituted alkyl group, an optionally substituted cycloalkyl group, an optionally substituted aryl group, or an optionally substituted heterocyclic group, with the proviso that $R^1$ and $R^2$ together with the adjacent phosphorus atom may form a 4- to 6-membered ring, or a salt thereof, which comprises converting a compound represented by the formula:

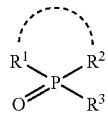

wherein each symbol is as defined above, or a salt thereof in a solvent in the presence of a borane reagent;

(2) The process according to the above (1), wherein $R^3$ is a hydrogen atom;

(3) The process according to the above (2), wherein $R^1$ and $R^2$ together with the adjacent phosphorus atom form a 5-membered ring;

(4) The process according to the above (1), wherein $R^1$ and $R^2$ are the same or different and independently represent a hydrogen atom, a halogen atom, an optionally substituted alkyl group, an optionally substituted cycloalkyl group, an optionally substituted aryl group, or an optionally substituted heterocyclic group with a proviso that $R^1$ and $R^2$ together with the adjacent phosphorus atom may form a 4- to 6-membered ring; and $R^3$ represents a halogen atom, an optionally substituted alkyl group, an optionally substituted cycloalkyl group, an optionally substituted aryl group, or an optionally substituted heterocyclic group;

(5) The process according to the above (4), wherein $R^1$ and $R^2$ together with adjacent phosphorus atom form a 4- or 6-membered ring;

(6) The process according to the above (2) or (4), wherein $R^1$ and $R^2$ are the same or different and independently represent an optionally substituted aryl group;

(7) The process according to the above (6), wherein $R^1$ and $R^7$ are the same or different and independently represent a phenyl optionally substituted with 1 to 5 lower alkyl groups, lower alkoxy groups, halogen atoms, mono-lower alkylamino groups, or di-lower alkylamino groups;

(8) The process according to the above (2) or (4), wherein $R^1$ and $R^2$ are the same or different and independently represent a lower alkyl group or a lower cycloalkyl group;

(9) The process according to the above (1), wherein the borane reagent is a borane-tetrahydrofuran complex; and the like.

BEST MODE FOR CARRYING OUT THE INVENTION

In the above formula, $R^1$, $R^2$, and $R^3$ are the same or different and independently represent a hydrogen atom, a halogen atom, an optionally substituted alkyl group, an optionally substituted cycloalkyl group, or an optionally substituted aryl group.

The "halogen atom" represented by $R^1$, $R^2$, and $R^3$ includes fluorine, chlorine, bromine, and iodine.

The alkyl group of the "optionally substituted alkyl group" represented by $R^1$, $R^2$, and $R^3$ includes lower alkyl groups (e.g. $C_{1-6}$ alkyl groups such as methyl, ethyl, propyl, isopropyl, butyl, isobutyl, sec-butyl, tert-butyl, pentyl, hexyl, and the like).

Examples of the substituent of the alkyl include (1) nitro, (2) nitroso, (3) cyano, (4) hydroxy, (5) lower alkoxy groups (e.g. $C_{1-6}$ alkoxy groups such as methoxy, ethoxy, propoxy, isopropoxy, butoxy, isobutoxy, sec-butoxy, tert-butoxy, pentoxy, hexyloxy, and the like), (6) formyl, (7) lower alkylcarbonyl groups (e.g. $C_{1-6}$ alkyl-carbonyl groups such as acetyl, propionyl, butyryl, isobutyryl, valeryl, isovaleryl, pivaloyl, and the like), (8) lower alkoxycarbonyl groups (e.g. $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, and the like), (9) carboxyl, (10) N-mono-lower alkylcarbamoyl groups (e.g. N-mono $C_{1-6}$ alkylcarbamoyl groups such as N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, and the like), (11) N,N-di-lower alkylcarbamoyl groups (e.g. N,N-di-$C_{1-6}$ alkylcarbamoyl groups such as N,N-dimethylcarbamoyl, N,N-diethylcarbamoyl, N,N-dipropylcarbamoyl, N,N-diisopropylcarbamoyl, N-ethyl-N-methylcarbamoyl, and the like), (12) halogen atoms (e.g. fluorine, chlorine, bromine, and iodine), (13) mono-lower alkylamino groups (e.g. mono-$C_{1-6}$ alkylamino groups such as methylamino, ethylamino, propylamino, isopropylamino, butylamino, isobutylamino, sec-butylamino, tert-butylamino, pentylamino, hexylamino, and the like), and (14) di-lower alkylamino groups (e.g. di-$C_{1-6}$ alkylamino groups such as dimethylamino, diethylamino, dipropylamino, diisopropylamino, dibutylamino, N-ethyl-N-methylamino, and the like). They may have 1 to 3 substituents selected from these groups at any possible positions.

The cycloalkyl group of the "optionally substituted cycloalkyl group" represented by $R^1$, $R^2$, and $R^3$ includes lower cycloalkyl groups (e.g. $C_{3-6}$ cycloalkyl groups such as cyclopropyl, cyclobutyl, cyclohexyl, and the like).

The substituent of the "cycloalkyl" includes the same substituents and the same number as those exemplified with respect to the above substituent of the "optionally substituted alkyl group".

The aryl group of the "optionally substituted aryl group" represented by $R^1$, $R^2$, and $R^3$ include $C_{6-10}$ aryl groups such as phenyl, 1-naphthyl, and 2-naphthy and the like, and ring-assembled aromatic hydrocarbons such as biphenyl, naphthyl-phenyl, and the like.

Examples of the substituent of the "aryl group" include (1) nitro, (2) nitroso, (3) cyano, (4) hydroxy, (5) lower alkyl groups (e.g. $C_{1-6}$ alkyl groups such as methyl, ethyl, propyl, isopropyl, butyl, isobutyl, sec-butyl, tert-butyl, pentyl, hexyl, and the like), (6) lower alkoxy groups (e.g. $C_{1-6}$ alkoxy groups such as methoxy, ethoxy, propoxy, isopropoxy, butoxy, isobutoxy, sec-butoxy, tert-butoxy, pentoxy, hexyloxy, and the like), (7) formyl, (8) lower alkylcarbonyl groups (e.g. $C_{1-6}$ alkyl-carbonyl groups such as acetyl, propionyl, butyryl, isobutyryl, valeryl, isovaleryl, pivaloyl, and the like), (9) lower alkoxycarbonyl groups (e.g. $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl, and the like), (10) carboxyl, (11) N-mono-lower alkylcarbamoyl groups (e.g. N-mono-$C_{1-6}$ alkylcarbamoyl groups such as N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, and the like), (12) N,N-di-lower alkylcarbamoyl groups (e.g. N,N-di-$C_{1-6}$ alkylcarbamoyl groups such as N,N-dimethylcarbamoyl, N,N-diethylcarbamoyl, N,N-dipropylcarbamoyl, N,N-diisopropylcarbamoyl, N-ethyl-N-methylcarbamoyl, and the like), (13) halogen atoms (e.g. fluorine, chlorine, bromine, and iodine), (14) mono-lower alkylamino groups (e.g. mono-$C_{1-6}$ alkylamino groups such as methylamino, ethylamino, propylamino, isopropylamino, butylamino, isobutylamino, sec-butylamino, tert-butylamino, pentylamino, hexylamino, and the like), (15) di-lower alkylamino groups (e.g. di-$C_{1-6}$ alkylamino groups such as dimethylamino, diethylamino, dipropylamino, diisopropylamino, dibutylamino, N-ethyl-N-methylamino, and the like), and (16) halogeno-lower alkyl groups (e.g. halogeno-$C_{1-6}$ alkyl groups such as fluoromethyl, difluoromethyl, trifluoromethyl, 2,2,2-trifluoroethyl, chloromethyl, dichloromethyl, trichloromethyl, and the like). They may have 1 to 5 substituents selected from these groups at any possible positions.

The heterocyclic group of the "optionally substituted heterocyclic group" represented by $R^1$, $R^2$, and $R^3$ includes 1-pyrrolyl, 2-pyrrolyl, 3-pyrrolyl, 1-imidazolyl, 2-imidazolyl, 4-imidazolyl, 5-imidazolyl, 1-pyrrolidinyl, 2-pyrrolidinyl, 3-pyrrolidinyl, pyrrolinyl, 1-imidazolidinyl, 2-imidazolidinyl, 3-imidazolidinyl, 4-imidazolidinyl, imidazolinyl, 2-pyridyl, 3-pyridyl, 4-pyridyl, pyradinyl, 2-pyrimidinyl 4-pyrimidinyl, 5-pyrimidinyl, 1-piperidyl, 2-piperidyl, 3-piperidyl, 4-piperidyl, 2-oxazolyl, 4-oxazolyl, 5-oxazolyl, 2-furyl, 3-furyl, 2-pyranyl, 3-pyranyl, 4-pyranyl, 5-pyranyl, 6-pyranyl, 1,3-dioxolan-2-yl, 1,3-dioxolan-4-yl, 1,4-dioxolan-2-yl, 1,4-dioxolan-3-yl, and the like.

The substituent of the "heterocyclic group" include the same substituents and the same number as those exemplified with respect to the above substituent of the "optionally substituted aryl group".

When $R^1$ and $R^2$ together with the adjacent phosphorus atom form a 4- to 6-membered ring, the compound (II) includes, for example, that having a structure represented by the following formula:

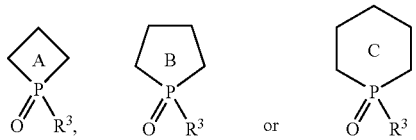

wherein the ring A, the ring B, and the ring C may have a substituent; and $R^3$ is as defined above. The substituent of the above exemplified ring include the same substituent and the same number as those exemplified with respect to the above substituent of the "optionally substituted aryl group".

Preferably, $R^1$ and $R^2$ are the same or different and independently represent an optionally substituted alkyl group, an optionally substituted cycloalkyl group, or an optionally substituted aryl group.

Among them, lower alkyl groups, lower cycloalkyl groups, or optionally substituted $C_{6-10}$ aryl groups are more preferable. In particular, phenyl groups optionally substituted with 1 to 5 lower alkyl groups, lower alkoxy groups, halogen atoms, mono-lower alkylamino or di-lower alkylamino groups are preferable. Specifically, phenyl groups optionally substituted with 1 to 3 lower alkyl groups, lower alkoxy groups, halogen atoms, mono-lower alkylamino or di-lower alkylamino groups are more preferable, A hydrogen atom is preferable for $R^3$.

Examples of the salts of the compound (I) and the compound (II) include salts with inorganic acids (e.g. hydrochloric acid, hydrobromic acid, nitric acid, sulfuric acid, phosphoric acid, and the like), and salts with organic acids (e.g. formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like). In the case the compounds (I) and (II) have acidic groups such as carboxyl groups and the like, salts with inorganic bases (e.g. alkali metals or alkaline earth metals such as sodium, potassium, calcium, magnesium, and the like, and ammonia) or with organic bases (e.g. trimethylamine, triethylamine, pyridine, picoline, ethanolamine, diethanolamine, triethanolamine, dicyclohexylamine, N,N'-dibenzylethylenediamine, and the like) can be used.

Examples of the "borane reagent" to be used in the present invention include borane-tetrahydrofuran complex, borane-dimethylsulfide complex, borane-amine complexes (e.g. borane-ammonia complex, borane-tert-butylamine complex, borane-dimethylamine complex, borane-triethylamine complex, borane-trimethylamine complex, borane-4-ethylmorpholine complex, borane-2,6-lutidine complex, borane-morpholine complex, borane-4-methylmorpholine complex, borane-4-phenylmorpholine complex, borane-piperazine complex, borane-pyridine complex, borane-N,N-diethylaniline complex, borane-N,N-diisopropylaniline complex, and the like), and the like. Among them, borane-tetrahydrofuran complex is preferable.

The process of the present invention is the reaction of the compound (II) or a salt thereof and a borane reagent in a solvent to obtain the compound (I) or a salt thereof.

The amount of the borane reagent to be used is about 0.5 to 10 moles, preferably about 3 to 5 moles relative to 1 mole of the compound (II).

The above-mentioned reaction can be carried out in an inert organic solvent or in an inert water-containing organic solvent. Examples of the organic solvent include hydrocarbons (e.g. hexane, pentane, cyclohexane, and the like), aromatic hydrocarbons (e.g. toluene, benzene, chlorobenzene, and the like), ethers (e.g. diisopropyl ether, diethyl ether, tetrahydrofuran, 1,4-dioxane, 1,2-dimethoxyethane, and the like), halogenated hydrocarbons (e.g. chloroform, dichloromethane, 1,2-dichloroethane, carbon tetrachloride, and the like), nitriles (e.g. acetonitrile, propionitrile, and the like), and the like. These solvents may be used alone or in form of a mixed solvent. Preferable examples of the solvents include aromatic hydrocarbons, ethers, and halogenated hydrocarbons. Further preferable examples include aromatic hydrocarbons (toluene and benzene).

The reaction temperature in the reaction is about 0 to 40° C., preferably about 20 to 30° C. The borane reagent is added to the reaction over 0 hour or longer, preferably about 0.5 hour or longer, further preferably about 2 hours or longer. Usually, the addition is completed within about 5 hours. The reaction time of the reaction is about 0.5 to 24 hours, preferably about 1 to 5 hours.

The product produced can be isolated from a reaction mixture according to a conventional method and easily purified by a separation means such as recrystallization, distillation, chromatography, and the like.

Hereinafter, the present invention will be illustrated more in detail with reference to examples and reference examples. However, the present invention is not limited thereto. In the examples, the following apparatuses were employed for measuring respective physical properties. $^1$H Nuclear magnetic resonance spectrometer ($^1$H-NMR): DPX300 (manufactured by Bruker): and an internal standard substance: tetramethylsilane. $^{13}$C-nuclear magnetic resonance spectrometer ($^{13}$C-NMR): DPX300 (manufactured by Bruker): and an internal standard substance: CDCl$_3$. $^{31}$P-Nuclear resonance spectrometer ($^{31}$P-NMR): DPX300 (manufactured by Bruker), an external standard substance: an aqueous 85% H$_3$PO$_4$ solution.

REFERENCE EXAMPLE 1

Di(p-tolyl)phosphine oxide

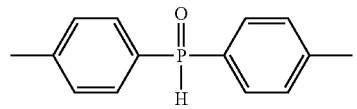

In a stream of nitrogen, a solution of magnesium (58.41 g, 3.48 equivalents), a slight amount of iodine and 1,2-dibromoethane in tetrahydrofuran (400 mL) was stirred at room temperature for 1 hour. After addition of a solution of p-bromotoluene (411.11 g, 3.48 equivalents) in tetrahydrofuran (2000 mL) at 22° C., the mixture was stirred at 40° C. for 1 hour. Then, after addition of a solution of diethyl phosphite (94.76 g, 0.69 mol) in tetrahydrofuran (160 mL) at 20° C., the mixture was stirred at 24° C. for 30 minutes. 6M-HCl (320 mL) was added thereto at 4° C., followed by further addition of water (320 mL) and toluene (1000 mL), and the resulting mixture was stirred at a room temperature for 30 minutes. The reaction mixture was separated into layers, and the organic layer was successively washed with water (320 mL), an aqueous 5% NaHCO$_3$ solution (320 mL) and an aqueous 5% NaCl solution (320 mL). The organic layer was filtered under reduced pressure, and the filtrate was concentrated under reduced pressure. The residue was recrystallized from n-hexane and dried (under reduced pressure at 40° C.) to obtain the titled compound (87.12 g, white powder). The yield was 54.8%.

$^1$H-NMR (300 MHz, CDCl$_3$, TMS) δ: 2.39 (s, 6H), 7.27-7.30 (m, 4H), 7.54 (s, 1H), 7.57 (s, 1H), 7.59 (s, 1H), 7.61 (s, 1H), 8.03 (d, 1H, J$_{H\text{-}P}$=477.6 Hz). $^{13}$C-NMR (75 MHz, CDCl$_3$, CDCl$_3$) δ: 23.01, 129.16, 130.53, 130.85, 131.02, 131.99, 132.15, 144.38, 144.41. $^{31}$P-NMR (121 MHz, CDCl$_3$, 85% H$_3$PO$_4$) δ: 22.67 (dquint, J$_{H\text{-}P}$=477.6 Hz, J$_{HCC\text{-}P}$=13.3 Hz).

REFERENCE EXAMPLE 2

Dinaphthylphosphine oxide

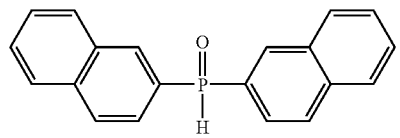

Under an argon atmosphere, a solution of magnesium (2.94 g, 2.00 equivalents), a slight amount of iodine and 1,2-dibromoethane in tetrahydrofuran (60 mL) was stirred at a room temperature for 1 hour. After addition of a solution of 2-bromonaphthalene (25.00 g, 2.00 equivalent) in tetrahydrofuran (20 mL) at 27° C., the mixture was stirred at 40° C. for 45 minutes. Then, after addition of a solution of diethyl phosphite (9.77 g, 0.06 mol) in tetrahydrofuran (10 mL) at −9° C., the mixture was stirred at 2° C. for 3 hours. Further, water (20 mL) was added thereto at −5° C., followed by further addition of toluene (60 mL) and 6M-HCl (20 mL). The resulting mixture was separated into layers, and the organic layer obtained was successively washed with an aqueous 5% NaHCO$_3$ solution and an aqueous 5% NaCl solution. The organic layer was dried over dehydrated magnesium sulfate and then spontaneously filtered, and the filtrate obtained was concentrated under reduced pressure. The residue was recrystallized from isopropyl ether/n-hexane and dried (under reduced pressure at 40° C.) to obtain the titled compound (9.621 g, white powder). The yield was 53.0%.

$^1$H-NMR (300 MHz, CDCl$_3$, TMS) δ: 7.49-7.64 (m, 6.5H), 7.86-7.95 (m, 6H), 8.40 (d, 2H, J=15.7 Hz), 9.15 (0.5H). $^{13}$C-NMR (75 MHz, CDCl$_3$, CDCl$_3$) δ: 125.07, 125.23, 127.13, 127.76, 127.93, 128.41, 128.81, 128.96, 132.43, 132.62, 132.82, 132.96, 135.05. $^{31}$P-NMR (121 MHz, CDCl$_3$, 85% H$_3$PO$_4$) δ: 22.99 (dquint, J$_{H\text{-}P}$=481.0 Hz, J$_{HCC\text{-}P}$=13.4 Hz).

REFERENCE EXAMPLE 3

Dicyclohexylphopshine oxide

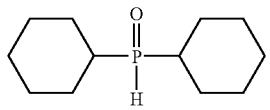

Under an argon atmosphere, bromocyclohexane (50.00 g, 2.00 equivalents) was added to a solution of magnesium (7.05 g, 1.93 equivalents) and a slight amount of iodine in tetrahydrofuran (70 mL) at 38 to 43° C., and the mixture was stirred at 5° C. for 1 hour. Then, after addition of diethyl phosphite (20.70 g, 0.15 mol) at 5° C., the mixture was stirred at 5° C. for 2 hours. Water (50 mL) was added thereto at 5° C., followed by further addition of 6 M-HCl (50 mL) and toluene (70 mL), and the resulting mixture was separated into layers. The organic layer obtained was successively washed with water, an aqueous 5% NaHCO$_3$ solution and an aqueous 5% NaCl solution, and the organic layer was dried over dehydrated magnesium sulfate and then spontaneously filtered. The filtrate was concentrated under reduced pressure. The residue was recrystallized from heptane and dried (under reduced pressure at 40° C.) to obtain the titled compound (10.5 g, white powder). The yield was 37.6%.

$^1$H-NMR (300 MHz, CDCl$_3$, TMS) δ: 1.25-1.98 (m, 22H), 6.28 (d, 1H, J$_{H-P}$=433.6 Hz). $^{31}$P-NMR (121 MHz, CDCl$_3$, 85% H$_3$PO$_4$) δ: 50.07 (d, J$_{H-P}$=433.5 Hz).

REFERENCE EXAMPLE 4

Di-p-methoxyphenylphosphine oxide

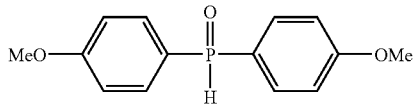

In a stream of nitrogen, a solution of magnesium (19.45 g, 4.00 equivalents), a slight amount of iodine and 1,2-dibromoethane in tetrahydrofuran (140 mL) was stirred at room temperature for 30 minutes. After addition of a solution of 1-boromo-4-methoxybenzene (151.47 g, 4.00 equivalents) in tetrahydrofuran (650 mL) at 25 to 30° C., the mixture was stirred at 40° C. for 1 hour. Then, a solution of diethyl phosphite (27.71 g, 0.20 mol) in tetrahydrofuran (60 mL) was added thereto at 25 to 30° C. Further 6M-HCl (110 mL) was added thereto at 0 to 5° C., followed by further addition of water (110 mL) and toluene (110 mL). The reaction mixture was separated into layers and the organic layer obtained was successively washed with water (110 mL), an aqueous 5% NaHCO$_3$ solution (110 mL) and an aqueous 5% NaCl solution (110 mL). The organic layer was dried over magnesium sulfate (25 g) and concentrated under reduced pressure. The residue was recrystallized from n-hexane and dried (in reduced pressure at 40° C.) to obtain the titled compound (15.71 g, white powder). The yield was 30.0%.

$^1$H-NMR (300 MHz, CDCl$_3$, TMS) δ: 3.85 (s, 6H), 6.98 (d, 2H, J=2.1 Hz), 7.01 (d, 2H, J=2.1 Hz), 7.57 (s, 1H), 7.60 (s, 1H), 7.62 (s, 1H), 7.65 (s, 1H), 8.03 (d, 1H, J$_{H-P}$=477 Hz). $^{13}$C-NMR (75 MHz, CDCl$_3$, CDCl$_3$) δ: 55.31, 114.29, 114.28, 122.27, 123.70, 132.51, 132.68, 162.87. $^{31}$P-NMR (121 MHz, CDCl$_3$, 85% H$_3$PO$_4$) δ: 21.19 (dq, J$_{H-P}$=477 Hz, J$_{H-CCP}$=13 Hz).

EXAMPLE 1

Diphenylphosphine-borane complex

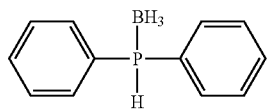

Under an argon atmosphere, 2 mL of toluene and 1 mL of tetrahydrofuran were added to diphenylphosphine oxide (0.4078 g, 2.0 mmol) at a room temperature (25° C.) and the mixture was stirred to obtain a suspension. Then, to the suspension was added 1.02 mol/L of a borane-tetrahydrofuran complex (6 mL, 3.06 equivalents). After the reaction solution was concentrated under reduced pressure, the residue was dissolved in toluene and purified by silica gel column chromatography (silica gel 25 g, toluene) and the desired fraction was concentrated under reduced pressure. The residue was recrystallized from n-hexane and dried (under reduced pressure at 40° C.) to obtain the titled compound (0.2982 g, transparent oil). The yield was 70.3%.

$^1$H-NMR (300 MHz, CDCl$_3$, TMS) δ: 0.51-1.75 (m, 3H), 6.31 (dq, 1H, J$_{H-P}$=378.7 Hz, J=7.0 Hz), 7.42-7.52 (m, 6H), 7.64-7.71 (m, 4H). $^{13}$C-NMR (75 MHz, CDCl$_3$, CDCl$_3$) δ: 125.50, 126.26, 128.66, 128.80, 131.28, 131.31, 132.54, 132.67. $^{31}$P-NMR (121 MHz, CDCl$_3$, 85% H$_3$PO$_4$) δ: 0.69-1.69 (m), 3.83-4.83 (m)

EXAMPLE 2

Di(p-tolyl)phosphine-borane complex

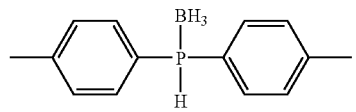

Under argon atmosphere, 32 mL of toluene was added to bis(p-tolyl)phosphine oxide synthesized in Reference Example 1 (7.11 g, 30.9 mmol) at a room temperature (25° C.) and the mixture was stirred to obtain a suspension. Then, to the suspension was added 1.02 mol/L of a borane-tetrahydrofuran complex (100 mL, 3.30 equivalents). After the reaction mixture was concentrated under reduced pressure, the residue was dissolved in toluene and purified by silica gel column chromatography (silica gel 25 g, toluene) and the desired fraction was concentrated under reduced pressure. The residue was recrystallized from n-hexane and dried (under reduced pressure at 40° C.) to obtain the titled compound (6.44 g, white powder). The yield was 91.4%.

$^1$H-NMR (300 MHz, CDCl$_3$, TMS) δ: 0.45-1.65 (m, 3H), 2.37 (s, 6H), 6.24 (dq, 1H, J$_{H-P}$=377.5 Hz, J=6.6 Hz), 7.22-7.25 (m, 4H), 7.49-7.56 (m, 4H). $^{31}$P-NMR (121 MHz, CDCl$_3$, 85% H$_3$PO$_4$) δ: -1.43--0.18 (m), 1.81-3.00 (m).

EXAMPLE 3

Dinaphthylphosphine-borane complex

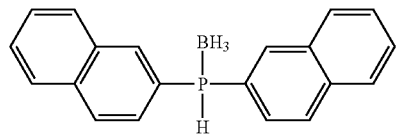

Under an argon atmosphere, 4 mL of toluene was added to dinaphthylphosphine oxide synthesized in Reference Example 2 (0.6061 g, 2.00 mmol) at a room temperature (25° C.) and the mixture was stirred to obtain a suspension. Then, to the suspension was added 1.02 mol/L of a borane-tetrahydrofuran complex (5 mL, 2.55 equivalents). The reaction mixture was purified by silica gel column chromatography (silica gel 15 g, toluene) and the desired fraction was concentrated under reduced pressure. The residue was dried (under reduced pressure at 40° C.) to obtain the titled compound (0.4577 g, white powder). The yield was 76.2%.

$^1$H-NMR (300 MHz, CDCl$_3$, TMS) δ: 0.60-1.85 (m, 3H), 6.56 (dq, 1H, J$_{H-P}$=378.7 Hz, J=6.9 Hz), 7.52-8.31 (m,

14H). $^{13}$C-NMR (75 MHz, CDCl$_3$, CDCl$_3$) δ: 124.40, 125.16, 128.53, 129.22, 129.31, 129.61, 129.96, 130.30, 130.43, 134.20, 134.36, 135.91, 135.94, 135.99, 136.14. $^{31}$P-NMR (121 MHz, CDCl$_3$, 85% H$_3$PO$_4$) δ: 1.10-2.21 (m), 3.92-4.95 (m).

EXAMPLE 4

Dicyclohexylphosphine-borane complex

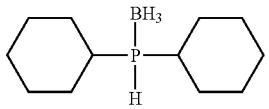

Under an argon atmosphere, 1 mL of toluene was added to dicyclohexylphosphine oxide synthesized in Reference Example 3 (0.1106 g, 0.50 mmol) at a room temperature (25° C.) to obtain a solution. Then, to the solution was added 1.02 mol/L of a borane-tetrahydrofuran complex (1.5 mL, 3.06 equivalents). The reaction mixture was concentrated under reduced pressure. The residue was dissolved in toluene and then purified by silica gel column chromatography (silica gel 10 g, toluene), and the desired fraction was concentrated under reduced pressure. The residue was recrystallized from n-hexane and dried (under reduced pressure at 40° C.) to obtain the titled compound (0.05 g, white powder). The yield was 4.3%.

$^1$H-NMR (300 MHz, CDCl$_3$, TMS) δ: 0.25-0.95 (m, 3H), 1.27-1.90 (m, 22H), 4.13 (dq, 1H, J$_{H-P}$=351.1 Hz, J=4.7 Hz). $^{31}$P-NMR (121 MHz, CDCl$_3$, 85% H$_3$PO$_4$) δ: 16.20-17.54 (m), 18.98-20.31 (m).

EXAMPLE 5

Di(p-methoxyphenyl)phosphine-borane complex

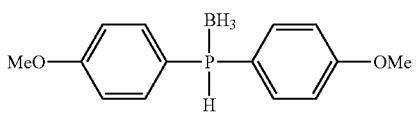

Under an argon atmosphere, 80 mL of toluene was added to di(p-methoxyphenyl)phosphine oxide synthesized in Reference Example 4 (13.11 g, 0.17 mmol) at a room temperature (25° C.) to obtain a solution. Then, to the solution was added 1.02 mol/L of a borane-tetrahydrofuran complex (165 mL, 3.30 equivalents) was added over 2 hours. After addition of silica gel (20 g), the reaction mixture as filtered and concentrated under reduced pressure. The resulting residue was recrystallized from n-hexane and dried (under reduced pressure at 40° C.) to obtain the titled compound (11.1 g, white powder). The yield was 85%.

$^1$H-NMR (300 MHz, CDCl$_3$, TMS) δ: 0.26-1.65 (m, 3H), 3.83 (s, 6H), 6.26 (dm, 1H, J$_{H-P}$=378 Hz), 6.94 (s, 1H), 6.95 (s, 1H), 6.96 (s, 1H), 6.97 (s, 1H), 7.55 (s, 1H), 7.57 (s, 1H), 7.58 (s, 1H), 7.61 (s, 1H). $^{13}$C-NMR (75 MHz, CDCl$_3$, CDCl$_3$) δ: 55.30, 114.59, 114.74, 116.84, 117.67, 134.43, 134.57, 162.23. $^{31}$P-NMR (121 MHz, CDCl$_3$, 85% H$_3$PO$_4$) δ: −4.5-(−3.2) (m), −1.6-0.4 (m).

INDUSTRIAL APPLICABILITY

Phosphine-borane complexes useful as production intermediates of phosphine ligands (e.g. 1,2-bis[(o-anisyl)phenylphosphino]ethane (DIPAMP); 1,2-bis(diphenylphosphino)propane (PROPHOS); 2,3-bis(diphenylphosphiono)butane (CHIRAPHOS); 2,4-bis(diphenylphosphino)pentane (BDPP) and the like) which can form complexes with transition metals (e.g. ruthenium, iridium, palladium, nickel, rhodium and the like) which can be used in asymmetric synthesis reactions, can be produced in a high yield under mild conditions according to the process of the present invention.

What is claimed is:

1. A process producing a phosphine-borane complex represented by the formula:

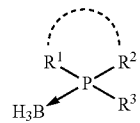

wherein R$^3$ is a hydrogen atom and wherein R$^1$ and R$^2$ are the same or different and independently represent a hydrogen atom, a halogen atom, an optionally substituted alkyl group, an optionally substituted cycloalkyl group, an optionally substituted aryl group, or an optionally substituted heterocyclic group, with the proviso that R$^1$ and R$^2$ together with the adjacent phosphorus atom may form a 4- to 6-membered ring, or a salt thereof, which comprises reacting a compound represented by the formula:

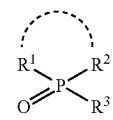

wherein each symbol is as defined above, or a salt thereof, with a borane reagent in a solvent.

2. The process according to claim 1, wherein R$^1$ and R$^2$ together with the adjacent phosphorus atom form a 5-membered ring.

3. The process according to claim 1, wherein R$^1$ and R$^2$ are the same or different and independently represent an optionally substituted aryl group.

4. The process according to claim 3, wherein R$^1$ and R$^2$ are the same or different and independently represent a phenyl optionally substituted with 1 to 5 lower alkyl groups, lower alkoxy groups, halogen atoms, mono-lower alkylamino groups, or di-lower alkylamino groups.

5. The process according to claim 1, wherein R$^1$ and R$^2$ are the same or different and independently represent a lower alkyl group or a lower cycloalkyl group.

6. The process according to claim 1, wherein the borane reagent is a borane-tetrahydrofuran complex.

* * * * *